US006225316B1

(12) United States Patent
Bös et al.

(10) Patent No.: US 6,225,316 B1
(45) Date of Patent: May 1, 2001

(54) 3-PHENYL-PYRIDINE-DERIVATIVES

(75) Inventors: Michael Bös, Montreal (CA); Guido Galley, Rheinfelden (DE); Thierry Godel, Basle (CH); Torsten Hoffmann, Lörrach (DE); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/505,359

(22) Filed: Feb. 16, 2000

(30) Foreign Application Priority Data

Feb. 24, 1999 (EP) .................................................. 99103503

(51) Int. Cl.[7] .......................... A61K 31/50; A61K 31/44; C07D 213/44; C07D 401/00
(52) U.S. Cl. .................... 514/252.18; 514/334; 546/262; 544/360
(58) Field of Search ................................ 546/276.7, 290, 546/307, 308, 262; 514/357, 351, 334

(56) References Cited

U.S. PATENT DOCUMENTS 4,174,209 * 11/1979 Taylor et al. .
5,972,938   10/1999 Rupniak et al. .

FOREIGN PATENT DOCUMENTS

95/16679   6/1995 (WO) .
95/18124   7/1995 (WO) .
95/23798   9/1995 (WO) .

OTHER PUBLICATIONS

R. Barker, *Reviews in the Neurosciences,* vol. 7, pp. 187–214 (1996).
J.Longmore et al., *Canadian J. Physiol. Pharmacol.,* vol. 75, pp. 612–621 (1997).
Mark S.Kramer et al., *Science,* vol. 281, pp. 1640–1645 (1998).
Carlo A. Maggi et al., *J.Auton. Pharmacol,* vol. 13, pp. 23–93 (1993).
Rudolph M. Navari et al., *New England J. of Medicine,* vol. 340, No. 3, pp. 190–195 (1999).
CA 101:191639b, "Studies on tertiary amine oxides. LXXVII. The pseudo–Gomberg reaction of 4– and 2–aminopyridine 1–oxides", vol. 101, p. 743, 1984.*

* cited by examiner

Primary Examiner—John Kight
Assistant Examiner—Binta Robinson
(74) Attorney, Agent, or Firm—George W. Johnston; Dennis P. Tramaloni

(57) ABSTRACT

The invention relates to compounds of the formula

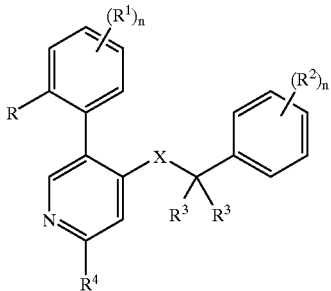

I wherein
  R is hydrogen, lower alkyl, lower alkoxy, halogen or trifluoromethyl;
  $R^1$ is hydrogen or halogen; or
  R and $R^1$ may be together —CH=CH—CH=CH—;
  $R^2$ is hydrogen, halogen, trifluoromethyl, lower alkoxy or cyano;
  $R^3$ is hydrogen, lower alkyl or form a cycloalkyl group;
  $R^4$ is hydrogen, —N($R^5$)$_2$, —N($R^5$)S(O)$_2$-lower alkyl, —N($R^5$)C(O)$R^5$ or a cyclic tertiary amine of the group

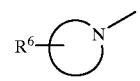

$R^5$ is, independently from each other, hydrogen, $C_{3-6}$-cycloalkyl, benzyl or lower alkyl;
  $R^6$ is hydrogen, hydroxy, lower alkyl, —N($R^5$)CO-lower alkyl, hydroxy-lower alkyl, cyano, —CHO or a 5- or 6- membered heterocyclic group, optionally bonded via an alkylene group,
  X is —C(O)N($R^5$)—, —(CH$_2$)$_m$O—, —(CH$_2$)$_m$N($R^5$)—, —N($R^5$)C(O)—, or —N($R^5$)(CH$_2$)$_m$—;
  n is 0–4; and
  m is 1 or 2;
and to pharmaceutically acceptable acid addition salts thereof.

It has been shown that the above mentioned compounds have a good affinity to the NK-1 receptor.

24 Claims, No Drawings

3-PHENYL-PYRIDINE-DERIVATIVES

BACKGROUND OF THE INVENTION

The neuropeptide receptor for Neurokinin 1 (substance P, NK-1) is widely distributed throughout the mammalian nervous system (especially brain and spinal ganglia), the circulatory system and peripheral tissues (especially the duodenum and jejunum) and are involved in regulating a number of diverse biological processes. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The central and peripheral actions of the mammalian tachykinin, substance P, have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (*Neurosci. Res.*, 1996, 7, 187–214), anxiety (*Can. J. Phys.*, 1997, 75, 612–621) and depression (*Science*, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is reviewed in "Tachykinin Receptor and Tachykinin Receptor Antagonists", *J. Auton. Pharmacol.*, 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

The compounds of formula I and their salts are characterized by valuable therapeutic properties. It has been surprisingly found that the compounds of the present invention are antagonists of the Neurokinin 1 (NK-1, substance P) receptor.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION OF THE INVENTION

The present invention relates to compounds of the general formula

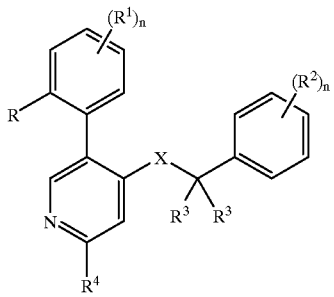

I wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is hydrogen, lower alkyl or form a cycloalkyl group;
$R^4$ is hydrogen, —N($R^5$)$_2$, —N($R^5$)S(O)$_2$-lower alkyl, —N($R^5$)C(O)$R^5$ or a cyclic tertiary amine of the group

$R^5$ is, independently from each other, hydrogen, $C_{3-6}$-cycloalkyl, benzyl or lower alkyl;
$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group,
X is —C(O)N($R^5$)—, —(CH$_2$)$_m$O—, —(CH$_2$)$_m$N($R^5$)—, —N($R^5$)C(O)— or —N($R^5$)(CH$_2$)$_m$—;
n is 0–4; and
m is 1 or 2;
and to pharmaceutically acceptable acid addition salts thereof.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–6 carbon atoms.

The term "cyclic tertiary amine" denotes, for example, pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

The term "5 or 6 membered heterocyclic group" denotes, for example pyridinyl, pyrimidinyl, oxadiazolyl, triazolyl, tetrazolyl, thiazolyl, thienyl, furyl, pyranyl, pyrrolyl, imidazolyl, pyrazolyl, isothiazolyl, piperazinyl or piperidyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Exemplary preferred are compounds, in which X is —C(O)N($R^5$)—, wherein $R^5$ is methyl, for example the following compounds:

N-(3,5-Bis-trifluoromethyl-benzyl)-N-methyl-3-o-tolyl-isonicotinamide,

N-(3,5-Bis-trifluoromethyl-benzyl)-3-(2-chlorophenyl)-N-methyl-isonicotinamide,

N-(3,5-Bis-trifluoromethyl-benzyl)-5-(2-chloro-phenyl)-N-methyl-2-(4-methyl-piperazin-1-yl)-isonicotinamide, N-(3,5-Bis-trifluoromethyl-benzyl)-5-(2-methoxy-phenyl)-N-methyl-2-(4-methyl-piperazin-1-yl)-isonicotinamide and N-(3,5-Bis-trifluoromethyl-benzyl)-N-methyl-2-(4-methyl-piperazin-1-yl)-5-phenyl-isonicotinamide.

N-(3,5-Dichloro-benzyl)-5-(2-methoxy-phenyl)-N-methyl-2-(4-methyl-piperazin-1-yl)-isonicotinamide Further preferred are compounds, in which X is —N($R^5$)C(O)—, wherein $R^5$ is methyl. Examples of such compounds are:

2-(3,5-Bis-trifluoromethyl-phenyl)-N-methyl-N-(3-o-tolyl-pyridin-4-yl)-isobutyramide, 2-(3,5-Bis-trifluoromethyl-phenyl)-N-[3-(2-chloro-phenyl)-pyridin-4-yl]-N-methyl-isobutyramide, 2-(3,5-Bis-trifluoromethyl-phenyl)-N-[3-(2-fluoro-phenyl)-pyridin-4-yl]-N-methyl-isobutyramide, 2-(3,5-Bis-trifluoromethyl-phenyl)-N-methyl-N-[3-(2-trifluoromethyl-phenyl)-pyridin-4-yl]-isobutyramide, 2-(3,5-Bis-trifluoromethyl-phenyl)-N-[3-(4-fluoro-2-methyl-phenyl)-pyridin-4-yl]-N-methyl-isobutyramide, 2-(3,5-Bis-trifluoromethyl-phenyl)-N-methyl-N-(3-naphthalen-1-yl-pyridin-4-yl)-isobutyramide and 2-(3,5-Bis-trifluoromethyl-phenyl)-N-[3-(2-methoxy-phenyl)-pyridin-4-yl]-N-methyl-isobutyramide The present compounds of formula I and their pharmaceutically acceptable salts can be prepared by methods known in the art, for example, by processes described below, which process comprises a) reacting a compound of formula

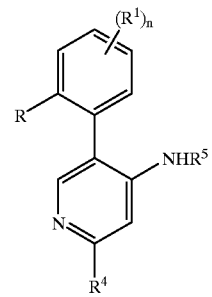

II with a compound of formula

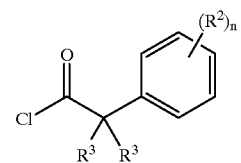

III to a compound of formula

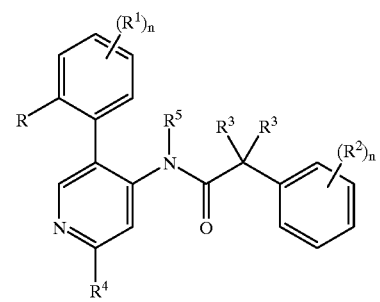

I-1 wherein R, $R^1$–$R^5$, and n have the significances given above, or b) reacting a compound of formula

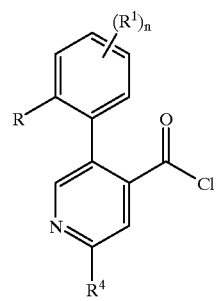

IV with a compound of formula

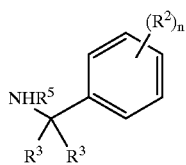

V to give a compound of formula

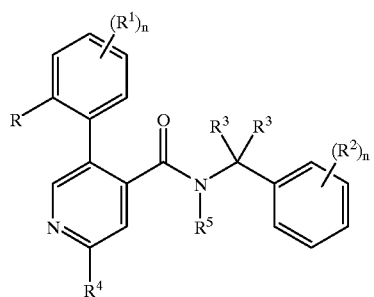

wherein $R^1$–$R^5$, R and n have the significances given above, or c) reducing a compound of formula

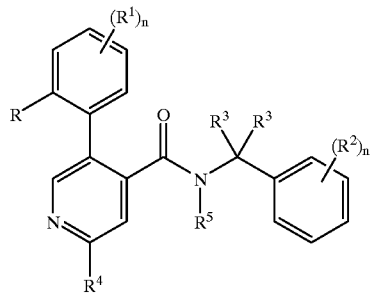

I-2 to a compound of formula

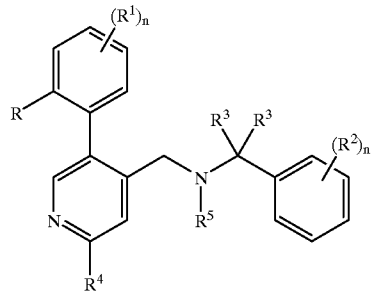

I-4 wherein the definitions of substituents are given above, or d) reacting a compound of formula

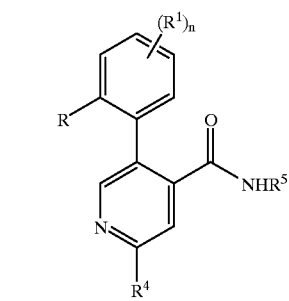

VI with a compound of formula

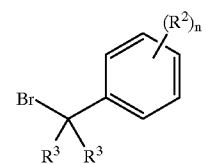

VII to a compound of formula

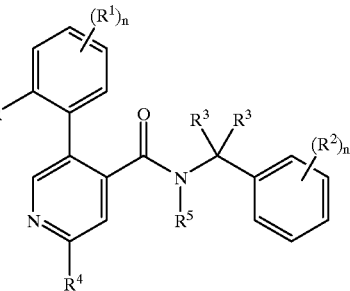

I-2 wherein the definitions of substituents are given above, or e) reacting a compound of formula

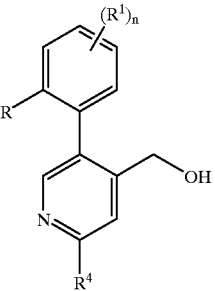

VIII with a compound of formula

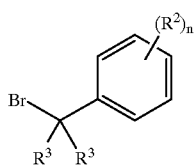

VII to a compound of formula

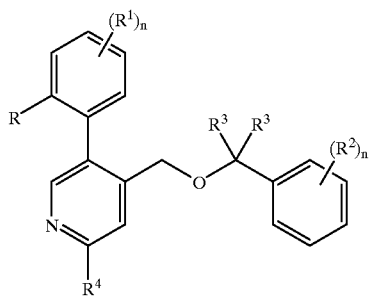

I-5 wherein the definitions of substituents are given above, or f) reducing a compound of formula

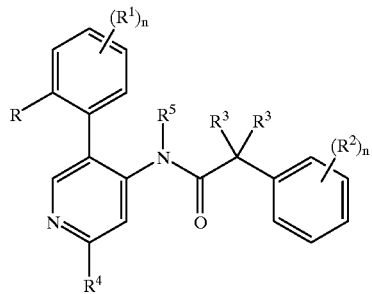

I-1 to a compound of formula

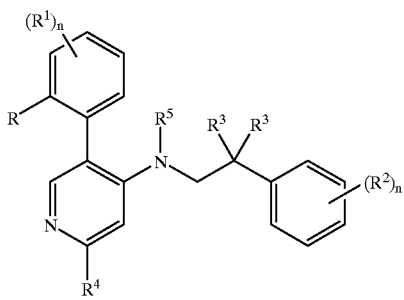

I-3 wherein the definitions of substituents are given above, or g) modifying one or more substituents $R^1$–$R^5$ or R within the definitions given above, and if desired, converting the compound obtained into a pharmaceutically acceptable acid addition salt.

In accordance with process variant a) a compound of formula II, for example methyl-(o-tolyl-pyridin-4-yl)-amine is deprotonated with KHMDS at 0° C. for 1 h and a compound of formula III, for example 2-(3,5-bis-trifluoromethyl-phenyl)-2-methyl-propionyl chloride is added and the mixture is stirred at room temperature. A typical solvent is N,N-dimethylformamide. The desired compound of formula I-1 is yielded after purification in good yields.

Process variant b) describes the reaction of a compound of formula IV with a compound of formula V to a compound of formula I-2. The reaction is carried out in conventional manner, for example in a solvent, such as a mixture of toluene and triethylamine. The mixture is refluxed for about 1 hour.

In accordance with process variant c) a compound of formula I-2 is reduced to a compound of formula I-4. This reaction is carried out with a reducing agent, such as $LiAlH_4$ or $BH_3.THF$, in conventional manner.

Process variant d) describes the reaction of a compound of formula VI with a compound of formula VII to a compound of formula I-2. This reaction is carried out by deprotonation of a compound of formula VI with KHMDS (potassium hexamethyldisilazide) and subsequent addition of a compound of formula VII. A suitable solvent is tetrahydrofuran. The reaction is carried out at room temperature.

In accordance with process variant e) a compound of formula I-5 is prepared. This reaction is carried out by deprotonation of a compound of formula VIII with NaH and subsequent addition of a compound of formula VII. This reaction is carried out in conventional manner.

A further method for the preparation of a compound of formula I is described in process variant f). A compound of formula I-1 is reduced to a compound of formula I-3 in conventional manner, for example with $LiAlH_4$ or $BH_3.THF$.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methanesulphonates, p-toluenesulphonates and the like are examples of such salts.

The following schemes 1–4 describe the processes for preparation of compounds of formula I in more detail. The starting materials of formulae VI, IX, XI, XIII, XII, XVI and XVII are known compounds are may be prepared according to methods known in the art.

In the schemes the following abbreviations have been used:

THF tetrahydrofuran

TMEDA N,N,N',N'-tetramethylethylene diamine

KHMDS potassium hexamethyldisilazide
DIBALH di-isobutylaluminum hydride
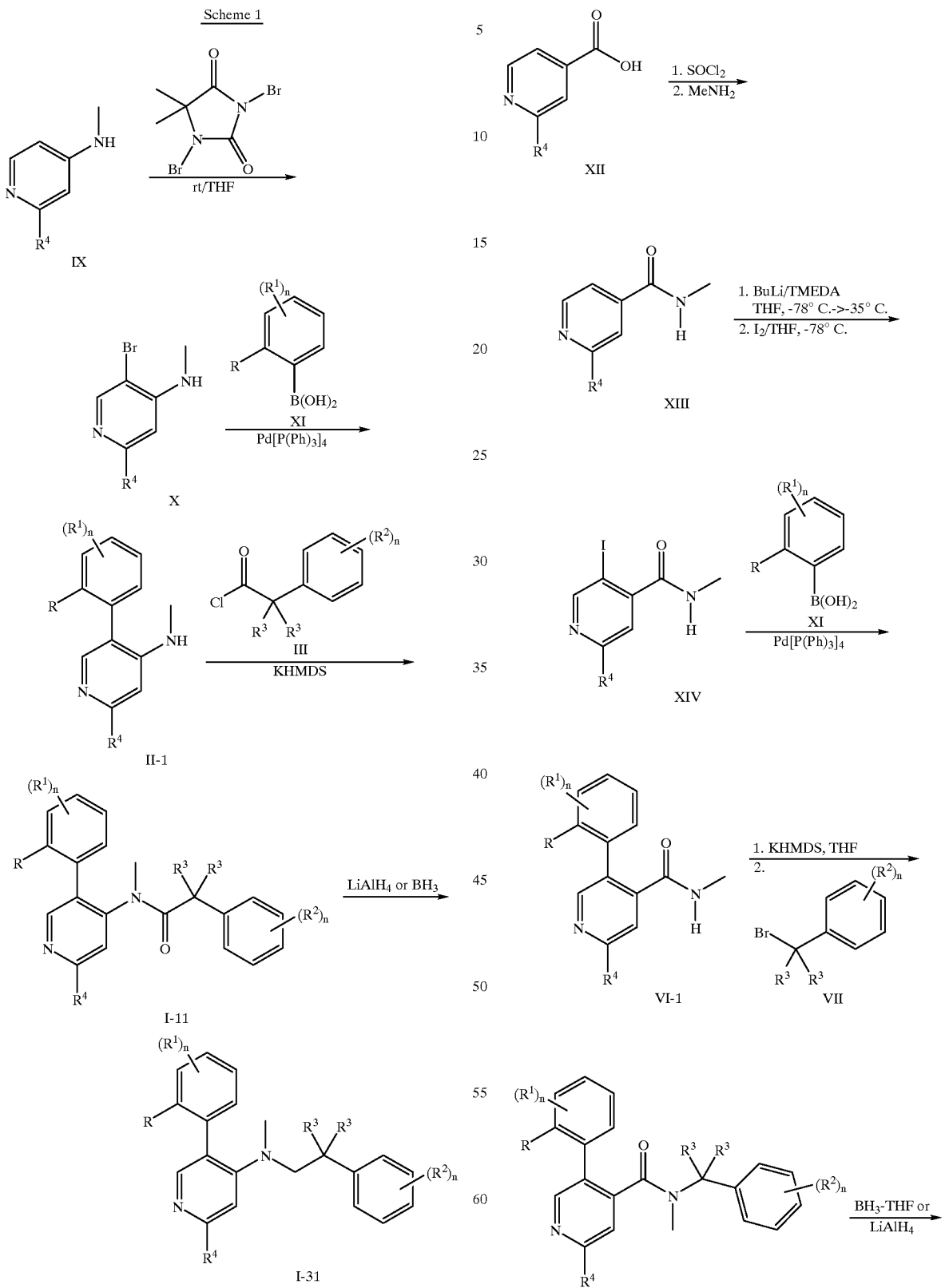

-continued
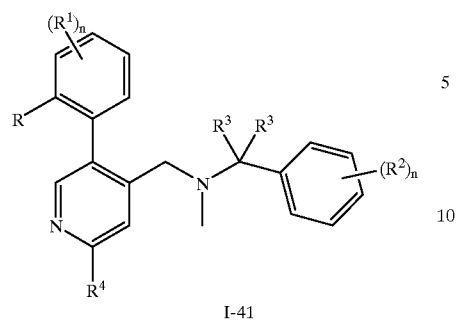
I-41
The definition of substituents is given above.
Scheme 3
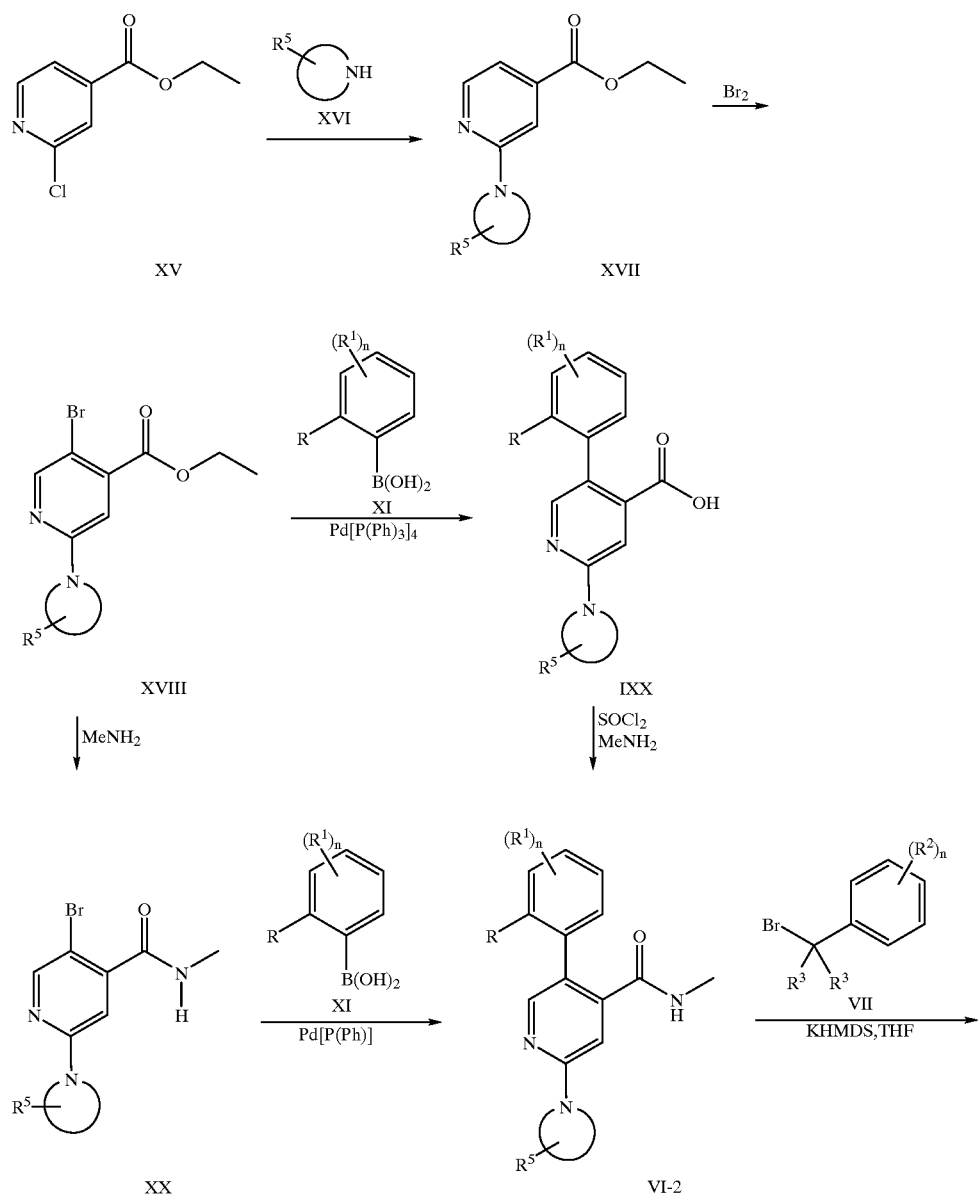

-continued

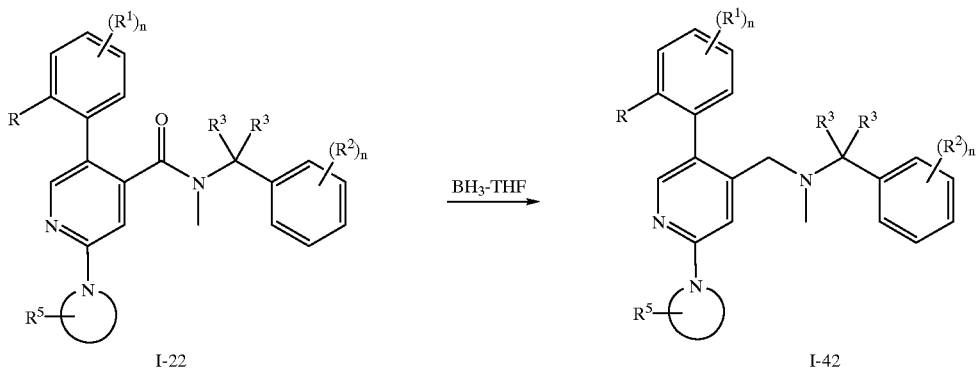

I-22

The definition of substituents is given above.

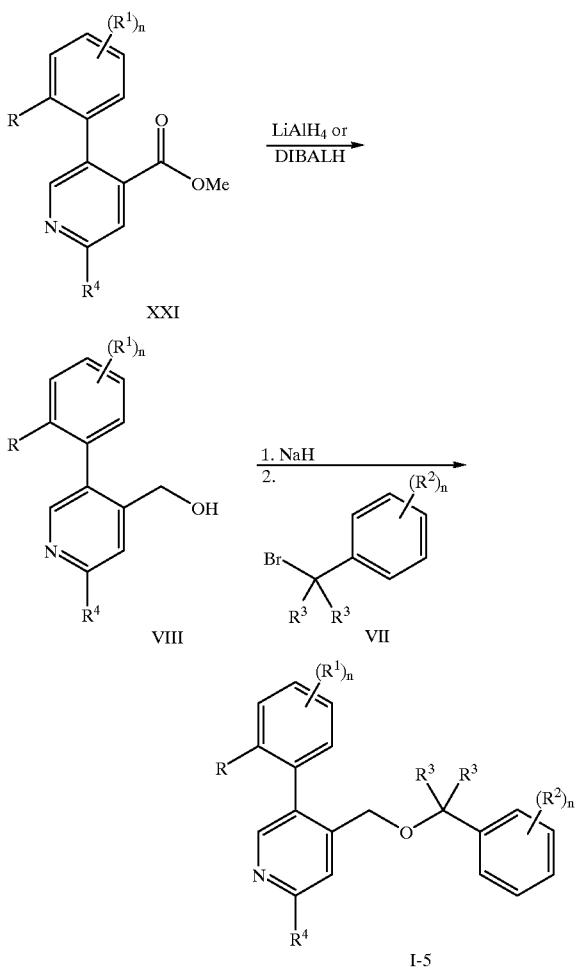

Scheme 4

I-5

The definition of substituents is given above.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension (1.25×10$^5$ cells/assay tube), 0.125 μl of buffer of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 7,50–9,00 for the preferred compounds. Examples of such compounds are the following:

| | |
|---|---|
| N-(3,5-Bis-trifluoromethyl-benzyl)-5-(2-methoxy-phenyl)-N-methyl-2-(4-methyl-piperazin-1-yl)-isonicotinamide | 7.80 |
| 2-(3,5-Bis-trifluoromethyl-phenyl)-N-[3-(2-methoxy-phenyl)-pyridin-4-yl]-N-methyl-isobutyramide | 7.86 |
| N-(3,5-Bis-trifluoromethyl-benzyl)-5-(2-chloro-phenyl)-N-methyl-2-(4-methyl-piperazin-1-yl)-isonicotinamide | 8.19 |
| 2-(3,5-Bis-trifluoromethyl-phenyl)-N-[3-(4-fluoro-2-methyl-phenyl)-pyridin-4-yl]-N-methyl-isobutyramide | 8.56 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

EXAMPLE 1

2-(3,5-Bis-trifluoromethyl-phenyl)-N-methyl-N-(3-o-tolyl-pyridin-4-yl)-isobutyramide hydrochloride (1:1)

a) (3-Bromo-pyridin-4-yl)-methyl-amine

To a solution of 10.6 g (98 mmol) 4-(N-methylamino)-pyridine in 200 ml tetrahydrofuran was added dropwise a solution of 14.0 g (49 mmol) 1,3-dibromo-5,5-dimethylhydantoin in 50 ml tetrahydrofuran at room temperature within 1.5 h. The solvent was removed and the residue was re-dissolved in ethyl acetate. The organic phase was washed four times with saturated sodium carbonate solution, dried (sodium sulfate) and evaporated. The residue was purified by flash chromatography to give 10.3 g (56%) of the title compound as white crystals.

MS m/e (%): 188 ($M^+$, 98), 187 (98), 186 ($M^+$, 100), 185 (96).

b) Methyl-(3-o-tolyl-pyridin-4-yl)-amine

A mixture of 1.26 g (6.75 mmol) (3-bromo-pyridin-4-yl)-methyl-amine, 13 ml toluene, 7 ml 2 N sodium carbonate solution, 234 mg (0.203 mmol) tetrakis(triphenylphosphine)palladium(0) and 1.01 g (7.43 mmol) o-tolylboronic acid was heated under argon at 80° C. for 12 h. After cooling to room temperature, the aqueous phase was separated and washed twice with toluene. The combined organic layers were washed with brine, dried (sodium sulfate) and evaporated. The residue was purified by flash chromatography to yield 164 mg (12%) of the title compound as a yellow oil.

MS m/e (%): 199 ($M+H^+$, 100).

c) 2-(3,5-Bis-trifluoromethyl-phenyl)-N-methyl-N-(3-o-tolyl-pyridin-4-yl)-isobutyramide To a solution of 140 mg (0.71 mmol) methyl-(3-o-tolyl-pyridin-4-yl)-amine in 1 ml N,N-dimethylformamide at 0° C. were added dropwise 0.71 ml (0.71 mmol) of 1 M potassium hexamethyldisilazide solution in tetrahydrofuran. Stirring was continued for 1 h at room temperature and the reaction mixture was cooled to 0° C. again. At this temperature, a solution of 270 mg (0.85 mmol) 2-(3,5-bis-trifluoromethyl-phenyl)-2-methyl-propionyl chloride in 0.5 ml tetrahydrofuran was added. After stirring for 18 h at room temperature, ethyl acetate was added and the organic phase was washed with brine, dried (magnesium sulfate) and evaporated. The residue was purified by flash chromatography to give 211 mg (58%) of the title compound as white foam.

MS m/e (%): 481 ($M+H^+$, 100).

d) 2-(3,5-Bis-trifluoromethyl-phenyl)-N-methyl-N-(3-o-tolyl-pyridin-4-yl)-isobutyramide hydrochloride (1:1)

To a solution of 82 mg (0.17 mmol) 2-(3,5-bis-trifluoromethyl-phenyl)-N-methyl-N-(3-o-tolyl-pyridin-4-yl)-isobutyramide in 5 ml diethyl ether were added under ice cooling 0.5 ml 3 N hydrochloric acid solution in diethyl ether. After stirring for 15 min at 0° C., the suspension was evaporated to dryness, re-suspended in 5 ml diethyl ether, filtered and dried in vacuo to give 89 mg (quantitative) of the title compound as white crystals.

MS m/e (%): 481 ($M+H^+$, 100).

EXAMPLE 2

2-(3,5-Bis-trifluoromethyl-phenyl)-N-[3-(2-chloro-phenyl)-pyridin-4-yl]-N-methyl-isobutyramide hydrochloride (1:1)

The title compound was obtained as white crystals in comparable yields according to the procedures described above for the preparation of Example 1 using o-chlorophenylboronic acid instead of o-tolylboronic acid in step b).

MS m/e (%): 503 ($M+H^+$, 100), 501 ($M+H^+$, 29).

EXAMPLE 3

2-(3,5-Bis-trifluoromethyl-phenyl)-N-[3-(2-fluoro-phenyl)-pyridin-4-yl]-N-methyl-isobutyramide hydrochloride (1:1)

The title compound was obtained as pale yellow crystals in comparable yields according to the procedures described above for the preparation of Example 1 using o-fluorophenylboronic acid instead of o-tolylboronic acid in step b).

MS m/e (%): 507 ($M+Na^+$, 6), 485 ($M+H^+$, 100).

EXAMPLE 4

2-(3,5-Bis-trifluoromethyl-phenyl)-N-methyl-N-[3-(2-trifluoromethyl-phenyl)-pyridin-4-yl]-isobutyramide The title compound was obtained as a white solid in comparable yields according to the procedures described above for the preparation of Example 1 using o-(trifluoromethyl)phenylboronic acid instead of o-tolylboronic acid in step b). No hydrochloride salt was prepared.

MS m/e (%): 534 ($M^+$, 2), 279 (100).

EXAMPLE 5

N-(3,5-Bis-trifluoromethyl-benzyl)-N-methyl-3-o-tolyl-isonicotinamide hydrochloride (1:1)

a) N-Methyl-isonicotin-amide

To 40 ml thionyl chloride at room temperature were added in portions 12.3 g (100 mmol) isonicotinic acid. After stirring overnight the solution was evaporated to dryness and the solid residue was added under ice cooling to 50 ml of a 33% solution of methyl amine in ethanol. After stirring for 3 h at room temperature the solid was filtered off and the filtrate evaporated to dryness. Stirring of the residue with 100 ml dichloromethane, filtration and evaporation of the solvent afforded 10.97 g (81.9%) of the title compound as off-white crystals. M.p. 104–106° C.

MS m/e (%): 136 ($M^+$, 60).

b) 3-Iodo-N-methyl-isonicotinamide

To a solution of 1.36 g (10 mmol) N-methyl-isonicotinamide in 20 ml tetrahydrofuran and 4.5 ml (30 mmol) N,N,N',N'-tetramethylethylenediamine at −70° C. were added 25 ml (40 mmol) 1.6 M n-butyl lithium solution in hexane. After stirring for 2 h at −10 to 0° C. a solution of 7.6 g iodine in 20 ml tetrahydrofuran was added dropwise at −70° C. Stirring was continued for 1 h at room temperature and 100 ml saturated sodium thiosulfate solution in water were added. The aqueous layer was separated and washed twice with ethyl acetate. The combined organic layers were washed with 1 N sodium hydroxide solution, brine, dried (magnesium sulfate) and evaporated. The residue was purified by chromatography to give 1.035 g (39%) of the title compound as white crystals. M.p. 132–133° C.

MS m/e (%): 262 (M$^+$, 100).

c) N-Methyl-3-o-tolyl-isonicotinamide

To a suspension of 450 mg (1.7 mmol) 3-iodo-N-methyl-isonicotinamide in 10 ml toluene were added successively 60 mg (0.05 mmol) tetrakis(triphenylphosphine)palladium (0), 2.5 ml 2 M sodium carbonate solution in water and 342 mg (2.5 mmol) o-tolylboronic acid. The mixture was heated under argon at 80° C. for 20 h. The aqueous layer was separated and washed twice with toluene. The combined organic layers were washed with brine, dried (magnesium sulfate) and evaporated. Chromatography of the residue afforded 341 mg (87%) of the title compound as a light yellow solid. M.p. 90–92° C.

MS m/e (%): 226 (M$^+$, 40).

d) N-(3,5-Bis-trifluoromethyl-benzyl)-N-methyl-3-o-tolyl-isonicotinamide

To a solution of 226 mg (1 mmol) N-methyl-3-o-tolyl-isonicotinamide in 10 ml tetrahydrofuran were added dropwise 1.3 ml (1.3 mmol) 1M potassium hexamethyldisilazide solution in tetrahydrofuran at room temperature. The white suspension was stirred for 30 min at room temperature and 0.18 ml (1 mmol) 3,5-bis(trifluoromethyl)benzyl bromide were added at the same temperature. The light brown suspension was stirred for 1 h and water was added. The aqueous layer was separated and washed with ethyl acetate. The combined organic layers were washed twice with brine, dried (magnesium sulfate) and evaporated. Chromatography of the residue afforded 440 mg (97%) of the title compound as a light brown oil.

MS m/e (%): 452 (M$^+$, 5).

e) N-(3,5-Bis-trifluoromethyl-benzyl)-N-methyl-3-o-tolyl-isonicotinamide hydrochloride (1:1)

To a solution of 440 mg N-(3,5-bis-trifluoromethyl-benzyl)-N-methyl-3-o-tolyl-isonicotinamide in 5 ml diethyl ether were added 5 ml 3 N hydrochloric acid solution in diethyl ether. After stirring for 10 min at room temperature, the solution was evaporated to dryness, dissolved in 3 ml diethyl ether and stirred for 1 h at −10° C. Filtration of the suspension afforded 376 mg (79%) of the title compound as white crystals. M.p. 186–188° C.

EXAMPLE 6

N-(3,5-Bis-trifluoromethyl-benzyl)-3-(2-chlorophenyl)-N-methyl-isonicotinamide hydrochloride (1:1)

The title compound was obtained as white crystals in comparable yields according to the procedures described above for the preparation of Example 5 using o-chlorophenylboronic acid instead of o-tolylboronic acid in step c). M.p. 196–198° C.

EXAMPLE 7

2-(3,5-Bis-trifluoromethyl-phenyl)-N-[3-(4-fluoro-2-methyl-phenyl)-pyridin-4-yl]-N-methyl-isobutyramide hydrochloride (1:1)

The title compound was obtained as white crystals in comparable yield according to the procedures described above for the preparation of Example 1 using 4-fluoro-2--methyl-phenylboronic acid instead of o-tolylboronic acid in step b).

MS m/e (%): 499 (M+H$^+$, 100).

EXAMPLE 8

2-(3,5-Bis-trifluoromethyl-phenyl)-N-methyl-N-(3-naphthalen-1-yl-pyridin-4-yl)-isobutyramide hydrochloride (1:1)

The title compound was obtained as white crystals in comparable yield according to the procedures described above for the preparation of Example 1 using 1-naphthylboronic acid instead of o-tolylboronic acid in step b).

MS m/e (%): 517 (M+H$^+$, 100).

EXAMPLE 9

2-(3,5-Bis-trifluoromethyl-phenyl)-N-[3-(2-methoxy-phenyl)-pyridin-4-yl]-N-methyl-isobutyramide hydrochloride (1:1)

The title compound was obtained as white crystals in comparable yield according to the procedures described above for the preparation of Example 1 using o-methoxyphenylboronic acid instead of o-tolylboronic acid in step b).

MS m/e (%): 497 (M+H$^+$, 100).

EXAMPLE 10

N-(3,5-Bis-trifluoromethyl-benzyl)-5-(2-chloro-phenyl)-N-methyl-2-(4-methyl-piperazin-1-yl)-isonicotinamide a) 2-(4-Methyl-piperazin-1-yl)-isonicotinic acid ethyl ester A solution of 5.56 g (30 mmol) 2-chloro-isonicotinic acid ethyl ester in 20 ml 1-methylpiperazine was heated for 5 hrs at 90° C. The solvent was evaporated and the residue purified by chromatography to give 3.72 g (50%) of the title compound as a yellow oil.

MS m/e (%): 249 (M$^+$, 20), 179 (100).

b) 5-Bromo-2-(4-methyl-piperazin-1-yl)-isonicotinic acid ethyl ester

A solution of 0.91 ml (17.7 mmol) Br$_2$ was added dropwise to a solution of 2.95 g (11.8 mmol) 2-(4-methyl-piperazin-1-yl)-isonicotinic acid ethyl ester in 20 ml dichloromethane at 0° C.–4° C. Stirring was continued at room temperature for 1 h and 50 ml saturated sodium bicarbonate solution in water was added. The aqueous layer was separated and washed twice with dichloromethane. The combined organic layers were dried (magnesium sulfate) and evaporated. The residue was purified by chromatography to give 1.45 g (37%) of the title compound as a pale yellow oil.

MS m/e (%): 327, 329 (M$^+$, 20), 70 (100).

c) 5-Bromo-N-methyl-2-(4-methyl-piperazin-1-yl)-isonicotinamide

A solution of 1.45 g (5.8 mmol) 5-bromo-2-(4-methyl-piperazin-1-yl)-isonicotinic acid ethyl ester in 25 ml methylamin (33% in ethanol) was heated in a high pressure vessel at 85° for 12 h. Evaporation of the solvent afforded 1.81 g (100%) of the title compound as yellow crystals. M.p. 122–125° C.

MS m/e (%): 312, 314 (M$^+$, 19), 242,244 (100).

d) 5-(2-Chloro-phenyl)-N-methyl-2-(4-methyl-piperazin-1-yl)-isonicotinamide

To a suspension of 1.20 g (3.83 mmol) 5-bromo-N-methyl-2-(4-methyl-piperazin-1-yl)-isonicotinamide in 15 ml toluene were added successively 0.135 g tetrakis (triphenylphosphine)palladium(0), 4 ml 2 M sodium carbonate solution in water and 0.72 g (4.6 mmol) o-chlorphenylboronic acid. The mixture was heated under argon at 80° C. for 18 h. The aqueous layer was separated and washed with toluene. The combined organic layers were washed with brine, dried (magnesium sulfate) and evaporated. Chromatography of the residue afforded 0.84 g (63%) of the title compound as a pale brown foam.

MS m/e (%): 345 (M+H$^+$, 100).

e) N-(3,5-Bis-trifluoromethyl-benzyl)-5-(2-chloro-phenyl)-N-methyl-2-(4-methyl-piperazin-1-yl)-isonicotinamide To a solution of 0.074 g (0.21 mmol) 5-(2-chloro-phenyl)-N-methyl-2-(4-methyl-piperazin-1-yl)-isonicotinamide in 5 ml tetrahydrofuran at −10° C. were added dropwise 0.29 ml (0.29 mmol) of 1 M potassium hexamethyldisilazide solution in tetrahydrofuran. Stirring was continued for ½ h at −10° C. At this temperature 0.42 ml 3.5-bis(trifluoromethyl)-benzylbromide were added. The reaction was quenched with water after 10 min and the mixture was extracted with three 15 ml portions of ethyl acetate. The combined organic layers were washed with brine, dried (magnesium sulfate) and evaporated. Chromatography of the residue afforded 0.113 g (92%) of the title compound as a pale yellow oil.

MS m/e (%): 571 (M+H$^+$, 100).

EXAMPLE 11

N-(3,5-Bis-trifluoromethyl-benzyl)-5-(2-methoxy-phenyl)-N-methyl-2-(4-methyl-piperazin-1-yl)-isonicotinamide The title compound was obtained as a colorless oil in comparable yield according to the procedures described above for the preparation of Example 10 using o-methoxyphenylboronic acid instead of o-chlorphenylboronic acid in step d).

MS m/e (%): 567 (M+H$^+$, 100).

EXAMPLE 12

N-(3,5-Bis-trifluoromethyl-benzyl)-N-methyl-2-(4-methyl-piperazin-1-yl)-5-phenyl-isonicotinamide The title compound was obtained as a colorless oil in comparable yield according to the procedures described above for the preparation of Example 10 using phenylboronic acid instead of o-chlorphenylboronic acid in step d).

MS m/e (%): 537 (M+H$^+$, 100).

EXAMPLE 13

N-(3,5-Dichloro-benzyl)-5-(2-methoxy-phenyl)-N-methyl-2-(4-methyl-piperazin-1-yl)-isonicotinamide The title compound was obtained as a colorless oil in comparable yield according to the procedures described above for the preparation of Example 10 using o-methoxyphenylboronic acid instead of o-chlorphenylboronic acid in step d), and 3,5-dichlorbenzylbromide instead of 3,5-bis(trifluormethyl)-benzylbromide in step e).

MS m/e (%): 500 (M+H$^+$, 100).

EXAMPLE 14

N-(3,5-Dichloro-benzyl)-N-methyl-2-(4-methyl-piperazin-1-yl)-5-phenyl-isonicotinamide The title compound was obtained as a colorless oil in comparable yield according to the procedures described above for the preparation of Example 10 using phenylboronic acid instead of o-chlorphenylboronic acid in step d), and 3,5-dichlorbenzylbromide instead of 3,5-bis(trifluormethyl)-benzylbromide in step e).

MS m/e (%): 470 (M+H$^+$, 100).

EXAMPLE 15

(3,5-Bis-trifluoromethyl-benzyl)-methyl-(3-o-tolyl-pyridin-4-ylmethyl)-amine

To a solution of 0.12 g (0.265 mmol) N-(3,5-bis-trifluoromethyl-benzyl)-N-methyl-3-o-tolyl-isonicotinamide in 3 ml tetrahydrofuran 1.6 ml of a 1M solution of BH$_3$ in tetrahydrofuran was added and the reaction mixture stirred for 16 h at 60° C. After addition of 2 ml 3M HCl in ether the reaction mixture was stirred for 3 h at 60° C. The solution was cooled to room temperature and 5 ml 3N sodium hydroxide solution and 10 ml ethyl acetate were added. Stirring was continued for ½ h, the phases separated and the aqueous phase extracted twice with 15 ml ethyl acatate. The combined organic layers were washed with brine, dried (magnesium sulfate) and evaporated. Chromatography of the residue afforded 0.30 g (25%) of the title compound as a pale yellow oil.

MS m/e (%): 439 (M+H$^+$, 100)

EXAMPLE 16

(3,5-Bis-trifluoromethyl-benzyl)-(3-o-tolyl-pyridin-4-ylmethyl)-amine hydrochloride (1:2)

a) 3-o-Tolyl-isonicotinic acid

To a suspension of 1.05 g (4.21 mmol) 3-iodo-isonicotinic acid in 15 ml dimethoxyethane were added successively 0.243 g tetrakis(triphenylphosphine)palladium(0), 4.2 ml 2 M sodium carbonate solution in water and 0.69 g (5.05 mmol) o-tolylboronic acid. The mixture was heated under argon at 80° C. for 18 h. After cooling to room temperature the phases were separated and the organic phase was washed twice with water (pH=9). The combined aqueous layers were than adjusted to pH=3 and extracted with five portions ethyl acetate. The combined organic layers were washed with brine, dried (magnesium sulfate) and evaporated. Chromatography of the residue afforded 0.68 g (75%) of the title compound as pale yellow crystals.

b) N-(3,5-Bis-trifluoromethyl-benzyl)-3-o-tolyl-isonicotinamide

To a solution of 0.28 g (1.17 mol) 3-o-tolyl-isonicotinic acid and 0.34 g (1.40 mmol) 3,5-bis(trifluoromethyl)benzylamine in 10 ml dichloromethane 0.38 ml N-methylmorpholine and 0.27 g (1.40 mmol) N-(3-dimethylaminopropyl)-N'-ethyl-carbodiimide hydrochloride were added and the mixture stirred for 12 h. The phases were separated, the water phase extracted with three portions of dichloromethane. The combined organic phases were dried (magnesium sulfate) and evaporated. Chromatography of the residue afforded 0.26 g (51%) of the title compound as a colorless oil.

MS m/e (%): 439 (M+H$^+$, 100)

c) (3,5-Bis-trifluoromethyl-benzyl)-(3-o-tolyl-pyridin-4-ylmethyl)-amine

To a solution of 0.26 g (0.59 mmol) N-(3,5-bis-trifluoromethyl-benzyl)-3-o-tolyl-isonicotinamide in 5 ml tetrahydrofuran 3.6 ml of a 1M solution of BH$_3$ in tetrahydrofuran was added and the reaction mixture stirred for 16 h at 60°. After addition of 5 ml 3M HCl in ether the reaction mixture was stirred for 3 h at 60° C. The solution was cooled to room temperature and 10 ml 3N sodium hydroxide solution and 10 ml ethyl acetate were added. Stirring was continued for ½ h, the phases separated and the aqueous phase extracted twice with 15 ml ethyl acatate. The combined organic layers were washed with brine, dried (magnesium sulfate) and evaporated. Chromatography of the residue afforded 0.13 g (51%) of the title compound as a pale yellow oil.

MS m/e (%): 425 (M+H$^+$, 100)

EXAMPLE 17

4-(3,5-Bis-trifluoromethyl-benzyloxymethyl)-3-o-tolyl-pyridine a) 3-o-Tolyl-pyridin-4-yl)-methanol A solution of 0.18 g (0.84 mmol) 3-o-tolyl-isonicotinic acid in 8 ml tetrahydrofuran was treated with 1.7 ml of a 1M solution of BH₃ in tetrahydrofuran. The reaction mixture was stirred for 4 h at 60° C., was allowed to cool and quenched by careful addition of 1.7 ml 3N sodium hydroxide solution. The reaction mixture heated for 12 h at 60° C. After addition of 10 ml water the reaction mixture was extracted three times with ethyl acetate. The combined organic layers were washed with brine, dried (magnesium sulfate) and evaporated. Chromatography of the residue afforded 0.82 g (49%) of the title compound as colorless crystals.

MS m/e (%): 199 (M⁺, 38), 180 (100).

b) 4-(3,5-Bis-trifluoromethyl-benzyloxymethyl)-3-o-tolyl-pyridine

A solution of 0.112 mg (0.56 mmol) 3-o-tolyl-pyridin-4-yl)-methanol and 0.11 ml (0.56 mmol) 3,5-(bistrifluormethyl)benzylbromide (97%) in 2 ml dioxane was added to a suspension of 94 mg potassium hydroxide in 1 ml dioxane. After stirring for 16 h the reaction mixture was diluted with 10 ml water and extracted three times with 20 ml ethyl acatate. The combined organic layers were washed with brine, dried (magnesium sulfate) and evaporated. Chromatography of the residue afforded 0.130 g (55%) of the title compound as a colorless oil.

MS m/e (%): 426 (M+H⁺, 100).

Table 1 sets for the subtituents for each compound of the previously described Examples.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |

TABLE 1

| Example No. | R | R¹ | R² | R³ | R⁴ | X |
|---|---|---|---|---|---|---|
| 1 | CH₃ | H | 3,5-CF₃ | CH₃/CH₃ | H | —N(CH₃)CO— |
| 2 | Cl | H | 3,5-CF₃ | CH₃/CH₃ | H | —N(CH₃)CO— |
| 3 | F | H | 3,5-CF₃ | CH₃/CH₃ | H | —N(CH₃)CO— |
| 4 | CF₃ | H | 3,5-CF₃ | CH₃/CH₃ | H | —N(CH₃)CO— |
| 5 | CH₃ | H | 3,5-CF₃ | H/H | H | —CON(CH₃)— |
| 6 | Cl | H | 3,5-CF₃ | H/H | H | —CON(CH₃)— |
| 7 | CH₃ | F | 3,5-CF₃ | CH₃/CH₃ | H | —N(CH₃)CO— |
| 8 | together —CH=CH—CH=CH— | | 3,5-CF₃ | CH₃/CH₃ | H | —N(CH₃)CO— |
| 9 | OCH₃ | H | 3,5-CF₃ | CH₃/CH₃ | H | —N(CH₃)CO— |
| 10 | Cl | H | 3,5-CF₃ | H/H | 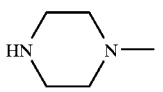 | —CON(CH₃)— |
| 11 | OCH₃ | H | 3,5-CF₃ | H/H | 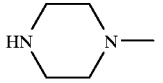 | —CON(CH₃)— |
| 12 | H | H | 3,5-CF₃ | H/H | 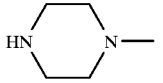 | —CON(CH₃)— |
| 13 | OCH₃ | H | 3,5-Cl | H/H | 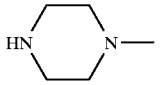 | —CON(CH₃)— |
| 14 | H | H | 3,5-Cl | H/H | 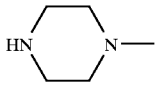 | —CON(CH₃)— |
| 15 | CH₃ | H | 3,5-CF₃ | H/H | H | —CH₂—N(CH₃)— |
| 16 | CH₃ | H | 3,5-CF₃ | H/H | H | —CH₂NH— |
| 17 | CH₃ | H | 3,5-CF₃ | H/H | H | —CH₂O— |

-continued

|  | mg/capsule |
|---|---|
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the general formula

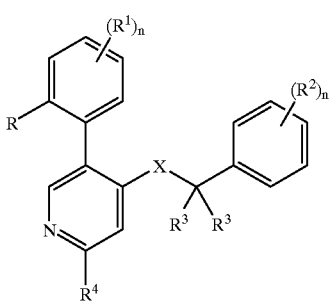

I wherein

R is hydrogen, lower alkyl, lower alkoxy, halogen or trifluoromethyl;

R$^1$ is hydrogen or halogen; or

R and R$^1$ may be together —CH=CH—CH=CH—;

R$^2$ is hydrogen, halogen, trifluoromethyl, lower alkoxy or cyano;

R$^3$ is hydrogen, lower alkyl or form a cycloalkyl group;

R$^4$ is hydrogen, —N(R$^5$)$_2$, —N(R$^5$)S(O)$_2$-lower alkyl, —N(R$^5$)C(O)R$^5$ or a cyclic tertiary amine of the group

R$^5$ is, independently from each other, hydrogen, C$_{3-6}$-cycloalkyl, benzyl or lower alkyl;

R$^6$ is hydrogen, hydroxy, lower alkyl, —N(R$^5$)CO-lower alkyl, hydroxy-lower alkyl, cyano, —CHO or a 5- or 6 membered heterocyclic group, optionally bonded via an alkylene group, X is —C(O)N(R$^5$)—, —(CH$_2$)$_m$O—, —(CH$_2$)$_m$N(R$^5$)—, —N(R$^5$)C(O)— or —N(R$^5$)(CH$_2$)$_m$—;

n is 0–4; and m is 1 or 2;

and pharmaceutically acceptable acid addition salts thereof.

2. A compound according to claim 1, wherein X is —C(O)N(R$^5$)— and R$^5$ is methyl.

3. A compound according to claim 2, N-(3,5-Bis-trifluoromethyl-benzyl)-N-methyl-3-o-tolyl-isonicotinamide.

4. A compound according to claim 2, N-(3,5-Bis-trifluoromethyl-benzyl)-3-(2-chlorophenyl)-N-methyl-isonicotinamide.

5. A compound according to claim 2, N-(3,5-Bis-trifluoromethyl-benzyl)-5-(2-chloro-phenyl)-N-methyl-2-(4-methyl-piperazin-1-yl)-isonicotinamide.

6. A compound according to claim 2, N-(3,5-Bis-trifluoromethyl-benzyl)-5-(2-methoxy-phenyl)-N-methyl-2-(4-methyl-piperazin-1-yl)-isonicotinamide.

7. A compound according to claim 2, N-(3,5-Bis-trifluoromethyl-benzyl)-N-methyl-2-(4-methyl-piperazin-1-yl)-5-phenyl-isonicotinamide.

8. A compound according to claim 2, N-(3,5-Dichloro-benzyl)-5-(2-methoxy-phenyl)-N-methyl-2-(4-methyl-piperazin-1-yl)-isonicotinamide.

9. A compound according to claim 1, wherein X is —N(R$^5$)C(O)— and R$^5$ is methyl.

10. A compound according to claim 9, 2-(3,5-Bis-trifluoromethyl-phenyl)-N-methyl-N-(3-o-tolyl-pyridin-4-yl)-isobutyramide.

11. A compound according to claim 9, 2-(3,5-Bis-trifluoromethyl-phenyl)-N-[3-(2-chloro-phenyl)-pyridin-4-yl]-N-methyl-isobutyramide.

12. A compound according to claim 9, 2-(3,5-Bis-trifluoromethyl-phenyl)-N-[3-(2-fluoro-phenyl)-pyridin-4-yl]-N-methyl-isobutyramide.

13. A compound according to claim 9, 2-(3,5-Bis-trifluoromethyl-phenyl)-N-methyl-N-[3-(2-trifluoromethyl-phenyl)-pyridin-4-yl]-isobutyramide.

14. A compound according to claim 9, 2-(3,5-Bis-trifluoromethyl-phenyl)-N-[3-(4-fluoro-2-methyl-phenyl)-pyridin-4-yl]-N-methyl-isobutyramide.

15. A compound according to claim 9, 2-(3,5-Bis-trifluoromethyl-phenyl)-N-methyl-N-(3-naphthalen-1-yl-pyridin-4-yl)-isobutyramide.

16. A compound according to claim 9, 2-(3,5-Bis-trifluoromethyl-phenyl)-N-[3-(2-methoxy-phenyl)-pyridin-4-yl]-N-methyl-isobutyramide.

17. A method of treating a disease related to the NK-1 receptor in a mammal comprising administering to said mammal a compound of formula I according to claim 1 and a pharmaceutically acceptable carrier in an amount which is effective in treating the disease related to the NK-1 receptor.

18. A pharmaceutical composition comprising a therapeutically effective amount of a compound of formula I according to claim 1 and a pharmaceutically acceptable carrier.

19. A process for preparing a compound of formula:

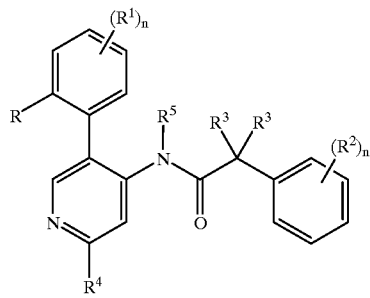

I-1 comprising reacting a compound of formula

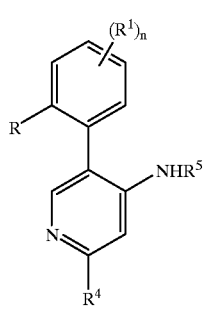

II with a compound of formula

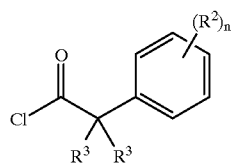

III wherein

R is hydrogen, lower alkyl, lower alkoxy, halogen or trifluoromethyl;

$R^1$ is hydrogen or halogen; or

R and $R^1$ may be together —CH=CH—CH=CH—;

$R^2$ is hydrogen, halogen, trifluoromethyl, lower alkoxy or cyano;

$R^3$ is hydrogen, lower alkyl or form a cycloalkyl group;

$R^4$ is hydrogen, —N($R^5$)$_2$, —N($R^5$)S(O)$_2$-lower alkyl, —N($R^5$)C(O)$R^5$ or a cyclic tertiary amine of the group

$R^5$ is, independently from each other, hydrogen, $C_{3-6}$-cycloalkyl, benzyl or lower alkyl; and n is 0–4.

20. A process for preparing a compound of formula:

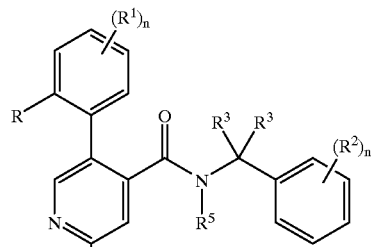

I-2 comprising reacting a compound of formula

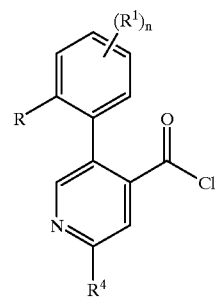

IV with a compound of formula

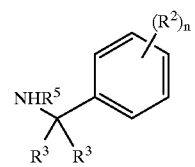

V wherein

R is hydrogen, lower alkyl, lower alkoxy, halogen or trifluoromethyl;

$R^1$ is hydrogen or halogen; or

R and $R^1$ may be together —CH=CH—CH=CH—;

$R^2$ is hydrogen, halogen, trifluoromethyl, lower alkoxy or cyano;

$R^3$ is hydrogen, lower alkyl or form a cycloalkyl group;

$R^4$ is hydrogen, —N($R^5$)$_2$, —N($R^5$)S(O)$_2$-lower alkyl, —N($R^5$)C(O)$R^5$ or a cyclic tertiary amine of the group

$R^5$ is, independently from each other, hydrogen, $C_{3-6}$-cycloalkyl, benzyl or lower alkyl; and n is 0–4.

21. A process for preparing a compound of formula:

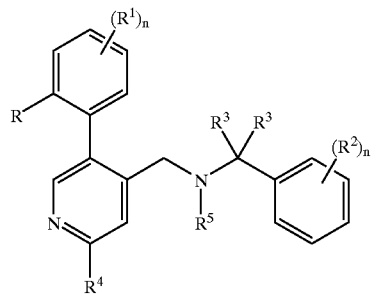

I-4 comprising reducing a compound of formula

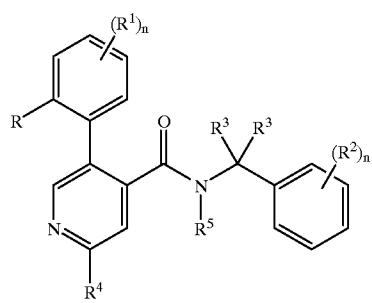

I-2 wherein

R is hydrogen, lower alkyl, lower alkoxy, halogen or trifluoromethyl;

$R^1$ is hydrogen or halogen; or

R and $R^1$ may be together —CH=CH—CH=CH—;

$R^2$ is hydrogen, halogen, trifluoromethyl, lower alkoxy or cyano;

$R^3$ is hydrogen, lower alkyl or form a cycloalkyl group;

$R^4$ is hydrogen, —N($R^5$)$_2$, —N($R^5$)S(O)$_2$-lower alkyl, —N($R^5$)C(O)$R^5$ or a cyclic tertiary amine of the group

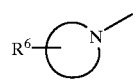

$R^5$ is, independently from each other, hydrogen, $C_{3-6}$-cycloalkyl, benzyl or lower alkyl;

$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group; and n is 0–4.

22. A process for preparing a compound of formula:

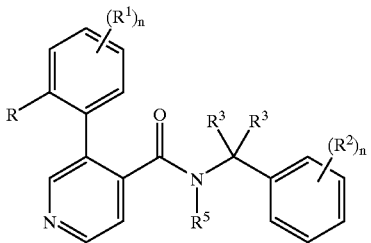

I-2 comprising reacting a compound of formula

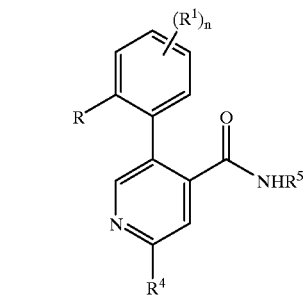

VI with a compound of formula

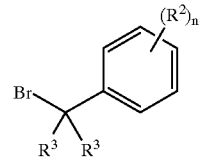

VII wherein

R is hydrogen, lower alkyl, lower alkoxy, halogen or trifluoromethyl;

$R^1$ is hydrogen or halogen; or

R and $R^1$ may be together —CH=CH—CH=CH—;

$R^2$ is hydrogen, halogen, trifluoromethyl, lower alkoxy or cyano;

$R^3$ is hydrogen, lower alkyl or form a cycloalkyl group;

$R^4$ is hydrogen, —N($R^5$)$_2$, —N($R^5$)S(O)$_2$-lower alkyl, —N($R^5$)C(O)$R^5$ or a cyclic tertiary amine of the group

$R^5$ is, independently from each other, hydrogen, $C_{3-6}$-cycloalkyl, benzyl or lower alkyl;

$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group; and n is 0–4.

23. A process for preparing a compound of formula:

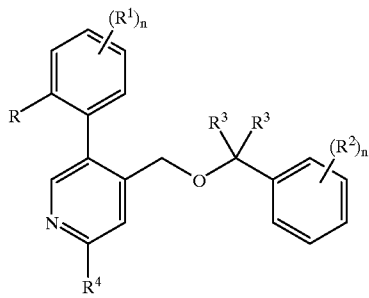

I-5 comprising reacting a compound of formula

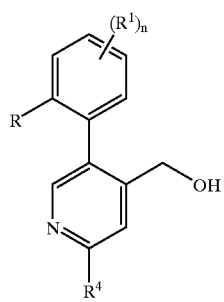

VIII with a compound of formula

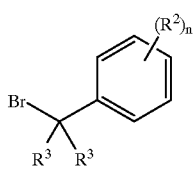

VII wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is hydrogen, lower alkyl or form a cycloalkyl group;
$R^4$ is hydrogen, —N($R^5$)$_2$, —N($R^5$)S(O)$_2$-lower alky, —N($R^5$)C(O)$R^5$ or a cyclic tertiary amine of the group

$R^5$ is, independently from each other, hydrogen, $C_{3-6}$-cycloalkyl, benzyl or lower alkyl;
$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group; and
n is 0–4.

24. A process for preparing a compound of formula:

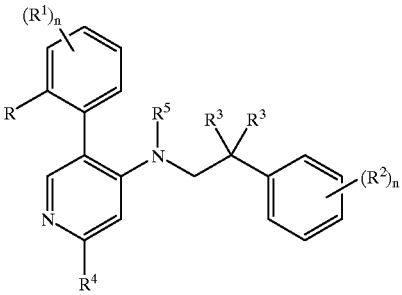

I-3 comprising reducing a compound of formula

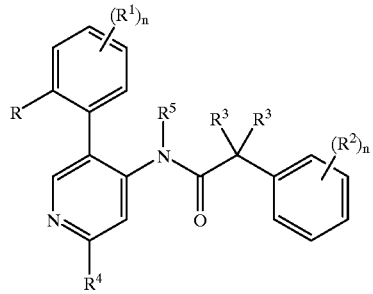

I-1 wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is hydrogen, lower alkyl or form a cycloalkyl group;
$R^4$ is hydrogen, —N($R^5$)$_2$, —N($R^5$)S(O)$_2$-lower alkyl, —N($R^5$)C(O)$R^5$ or a cyclic tertiary amine of the group

$R^5$ is, independently from each other, hydrogen, $C_{3-6}$-cycloalkyl, benzyl or lower alkyl;
$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group; and
n is 0–4.

* * * * *